United States Patent
von Hoffmann

(10) Patent No.: US 6,312,374 B1
(45) Date of Patent: Nov. 6, 2001

(54) RADIOACTIVE WIRE PLACEMENT CATHETER

(75) Inventor: Gerard von Hoffmann, Trabuco Canyon, CA (US)

(73) Assignee: Progenix, LLC, Trabuco Canyon, CA (US)

( * ) Notice: Subject to any disclaimer, the term of this patent is extended or adjusted under 35 U.S.C. 154(b) by 0 days.

(21) Appl. No.: 09/407,269

(22) Filed: Sep. 29, 1999

Related U.S. Application Data

(63) Continuation-in-part of application No. 09/299,177, filed on Apr. 23, 1999, which is a continuation-in-part of application No. 09/261,264, filed on Mar. 3, 1999, which is a division of application No. 08/813,822, filed on Mar. 6, 1997, now Pat. No. 5,879,324.

(51) Int. Cl.[7] ............................ A61N 5/00
(52) U.S. Cl. ............................ 600/3
(58) Field of Search .............. 600/1–8; 604/49, 604/43, 51–53, 57, 59, 62, 131, 140, 141, 149, 150, 191, 218, 248; 606/7, 194

(56) References Cited

U.S. PATENT DOCUMENTS

| | | |
|---|---|---|
| 4,406,656 | 9/1983 | Hattler et al. . |
| 4,496,347 | 1/1985 | MacLean et al. . |
| 4,771,778 | 9/1988 | Mar . |
| 4,773,901 | 9/1988 | Norton . |
| 4,798,593 | 1/1989 | Iwatschenko . |
| 4,808,164 | 2/1989 | Hess . |
| 4,820,349 | 4/1989 | Saab . |
| 4,824,435 | 4/1989 | Giesy et al. . |
| 4,884,573 | 12/1989 | Wijay et al. . |
| 5,047,045 | 9/1991 | Amey et al. . |
| 5,053,004 | 10/1991 | Markel et al. . |
| 5,199,939 | 4/1993 | Dake et al. . |
| 5,203,338 | 4/1993 | Jang . |
| 5,213,561 | 5/1993 | Weinstein et al. . |
| 5,219,335 | 6/1993 | Willard et al. . |
| 5,242,396 | 9/1993 | Evard . |
| 5,254,090 | 10/1993 | Lombardi et al. . |
| 5,255,668 | 10/1993 | Umeda . |
| 5,269,755 | 12/1993 | Bodicky . |
| 5,290,247 | 3/1994 | Crittenden . |
| 5,306,247 | 4/1994 | Pfenninger . |
| 5,318,532 * | 6/1994 | Frassica ............................ 604/96 |
| 5,354,257 | 10/1994 | Roubin et al. . |
| 5,364,357 | 11/1994 | Aase . |
| 5,370,615 | 12/1994 | Johnson . |
| 5,411,466 | 5/1995 | Hess . |
| 5,411,477 | 5/1995 | Saab . |
| 5,464,398 | 11/1995 | Haindl . |
| 5,470,322 | 11/1995 | Horzewski et al. . |
| 5,472,418 | 12/1995 | Palestrant . |
| 5,474,537 | 12/1995 | Solar . |
| 5,480,383 | 1/1996 | Bagaoisan et al. . |
| 5,484,384 | 1/1996 | Fearnot . |
| 5,484,408 | 1/1996 | Burns . |
| 5,498,249 | 3/1996 | Quinn . |

(List continued on next page.)

FOREIGN PATENT DOCUMENTS

| | | |
|---|---|---|
| 0 476 807 A1 | 3/1992 | (EP) . |
| 1318235 A1 | 6/1987 | (SU) . |
| WO 92/09326 | 6/1992 | (WO) . |
| WO 93/15785 | 8/1993 | (WO) . |
| WO 99/24116 | 5/1999 | (WO) . |

*Primary Examiner*—Robert L. Nasser
*Assistant Examiner*—Brian Szmal
(74) *Attorney, Agent, or Firm*—Knobbe, Martens, Olson & Bear, LLP

(57) ABSTRACT

Disclosed is a closed lumen catheter for facilitating placement of a radiation source within a vessel. A distal portion of at least a first lumen and a second lumen are separated by a moveable wall, allowing a reduced catheter shaft profile. Centering structures, such as one or more inflatable balloons, with perfusion, may be added. Methods are also disclosed.

28 Claims, 4 Drawing Sheets

U.S. PATENT DOCUMENTS

| | | |
|---|---|---|
| 5,499,973 | 3/1996 | Saab . |
| 5,503,613 | 4/1996 | Weinberger . |
| 5,533,968 | 7/1996 | Muni et al. . |
| 5,540,659 | 7/1996 | Teirstein . |
| 5,549,552 | 8/1996 | Peters et al. . |
| 5,549,553 | 8/1996 | Ressemann et al. . |
| 5,569,195 | 10/1996 | Saab . |
| 5,569,201 | 10/1996 | Burns . |
| 5,578,010 | 11/1996 | Ashby . |
| 5,587,125 | 12/1996 | Roychowdhury . |
| 5,599,325 | 2/1997 | Ju et al. . |
| 5,601,539 | 2/1997 | Corso, Jr. . |
| 5,616,114 | 4/1997 | Thornton et al. . |
| 5,618,266 | 4/1997 | Liprie . |
| 5,620,417 | 4/1997 | Jang et al. . |
| 5,683,345 * | 11/1997 | Waksman et al. ................ 600/3 |
| 5,728,067 | 3/1998 | Enger . |
| 5,772,642 | 6/1998 | Ciamacco, Jr. et al. . |
| 5,782,740 | 7/1998 | Schneiderman . |
| 5,797,948 | 8/1998 | Dunham . |
| 5,833,593 | 11/1998 | Liprie . |
| 5,840,064 | 11/1998 | Liprie . |
| 5,851,171 | 12/1998 | Gasson . |
| 5,855,546 | 1/1999 | Hastings et al. . |
| 5,857,956 | 1/1999 | Liprie . |
| 5,868,706 | 2/1999 | Cox . |
| 5,879,324 * | 3/1999 | von Hoffmann ................ 604/49 |
| 5,910,101 | 6/1999 | Andrews et al. . |
| 5,924,973 | 7/1999 | Weinberger . |
| 5,938,582 | 8/1999 | Ciamacco, Jr. et al. . |
| 5,947,889 | 9/1999 | Hehrlein . |
| 5,951,458 | 9/1999 | Hastings et al. . |
| 6,007,517 | 12/1999 | Anderson . |
| 6,024,690 | 2/2000 | Lee et al. . |
| 6,045,495 | 4/2000 | Weinberger . |
| 6,069,713 | 5/2000 | Urick et al. . |
| 6,074,338 | 6/2000 | Popowski et al. . |
| 6,077,213 | 6/2000 | Ciezki et al. . |
| 6,099,454 | 8/2000 | Hastings et al. . |
| 6,106,454 | 8/2000 | Berg et al. . |
| 6,117,386 | 9/2000 | Stiger . |

* cited by examiner

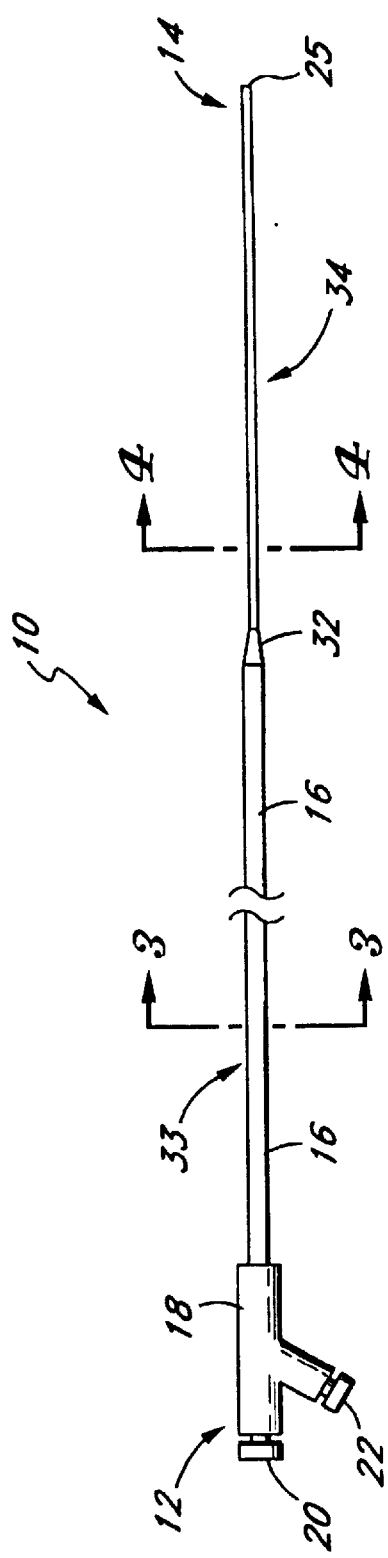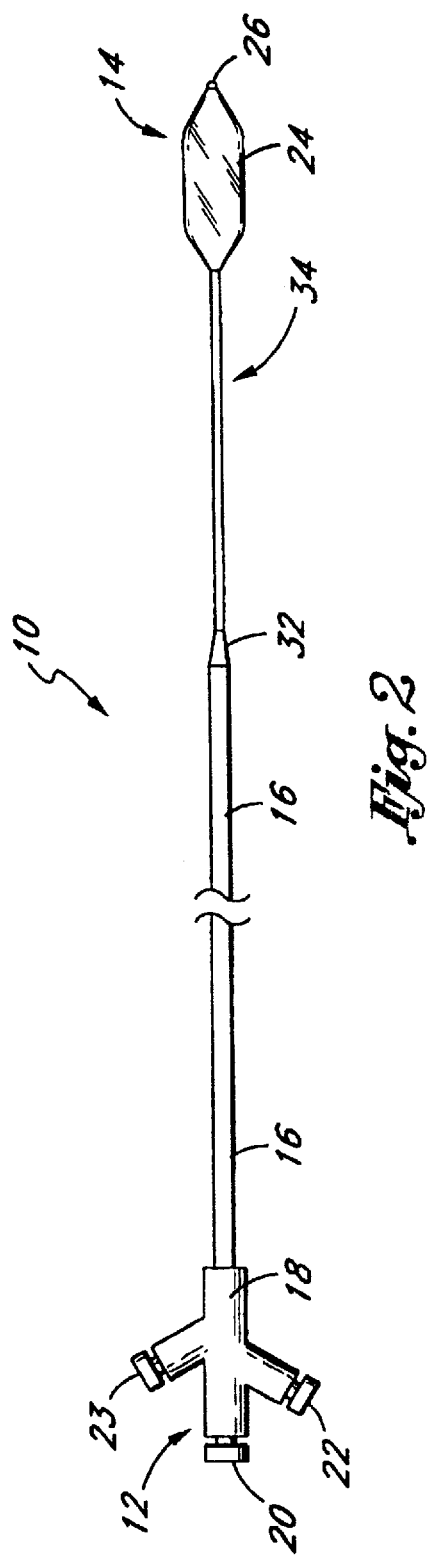
Fig. 1
Fig. 2

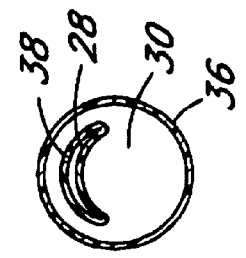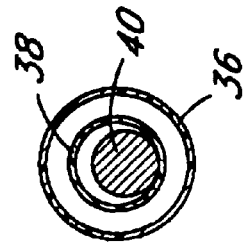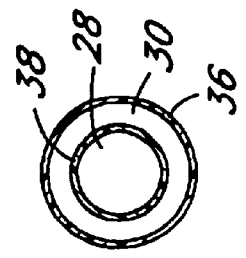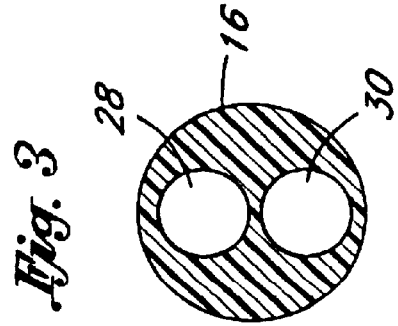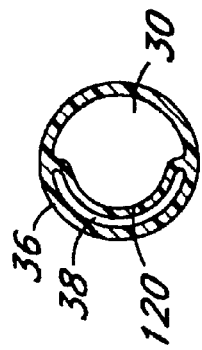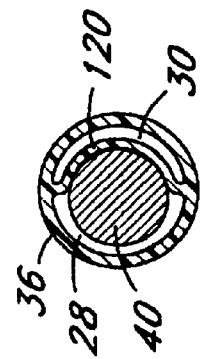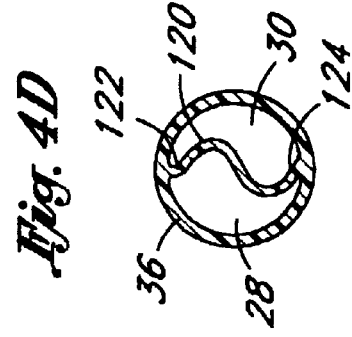

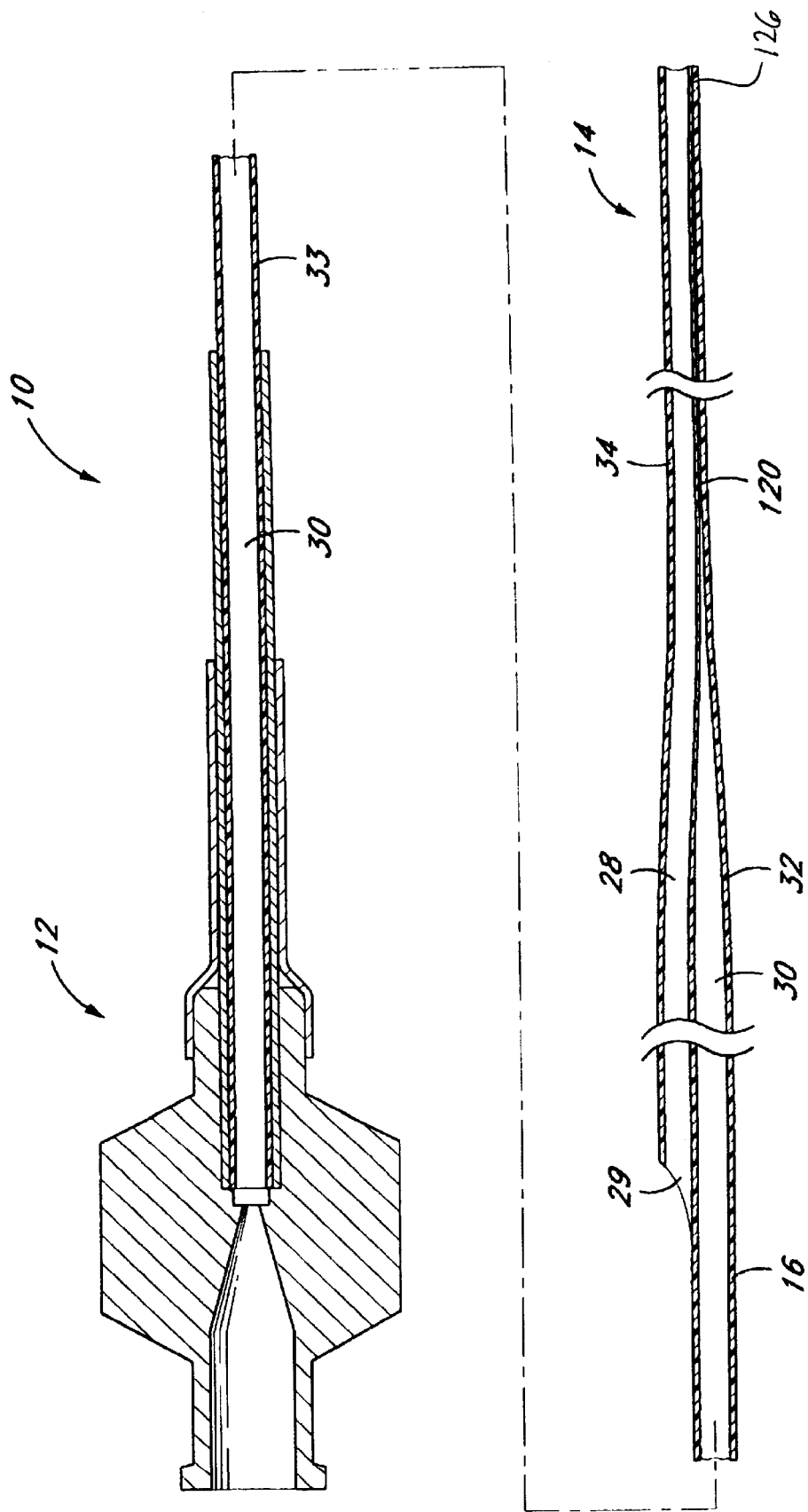

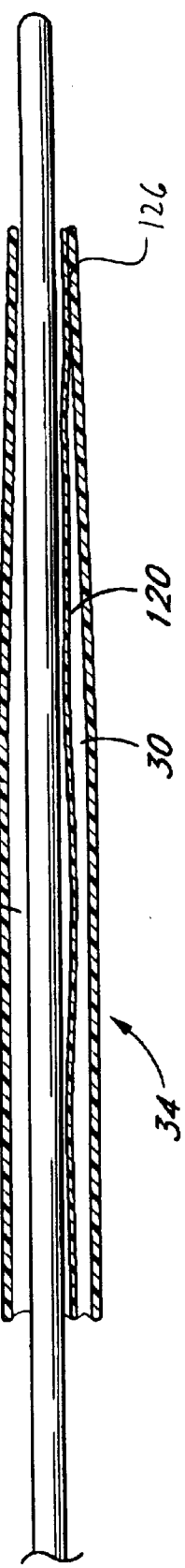
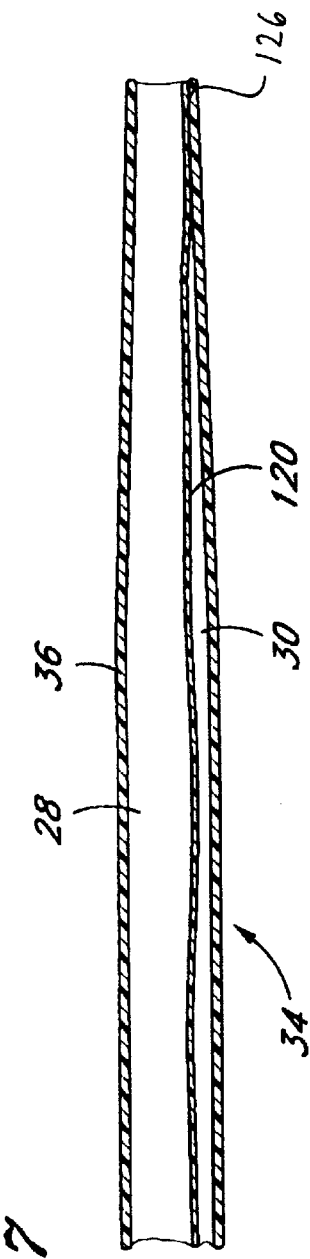
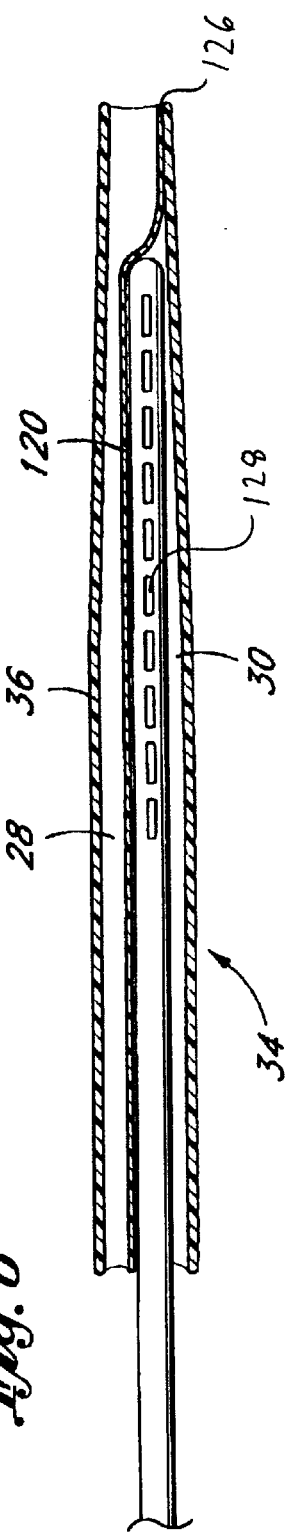

US 6,312,374 B1

RADIOACTIVE WIRE PLACEMENT CATHETER

This application is a continuation-in-part of application Ser. No. 09/299,177, filed Apr. 23, 1999, which is a continuation-in-part of application Ser. No. 09/261,264 filed Mar. 3, 1999, which is a division of application Ser. No. 08/813,822 filed Mar. 6, 1997, now U.S. Pat. No. 5,879,324.

BACKGROUND OF THE INVENTION

The present invention relates to radiation delivery catheters for percutaneous transluminal use. More particularly, the present invention relates to low profile catheter shaft designs for facilitating placement and centering of a radiation delivery wire within a body lumen.

A wide variety of interventional procedures have been developed which require access to remote parts of the vascular system. One increasingly utilized coronary revascularization procedure, for example, is percutaneous transluminal coronary angioplasty (PTCA). In a typical PTCA procedure, a guiding catheter having a prebent distal tip is percutaneously introduced at a remote location such as the femoral artery using a conventional Seldinger technique. The guide catheter is advanced retrograde until it reaches the ascending aorta with the distal tip seated in the ostium of a desired coronary artery. Steering is accomplished during transluminal advancement by torquing the proximal end of the guide catheter as needed until the distal tip is positioned in the ostium.

An elongate, flexible guidewire is then advanced through and out the distal end of the guide catheter, and negotiated through the tortuous vasculature of the coronary arteries until it crosses a lesion to be dilated. A dilatation catheter is thereafter advanced along the guidewire until the dilatation balloon is positioned within the lesion.

Once properly positioned, the balloon is inflated one or more times to an inflation pressure on the order of six to twelve atmospheres or higher to dilate the lesion. Balloon catheters sized for the coronary arteries may inflate to a diameter in the range of from about 2 mm to about 4 mm. Following dilatation, the balloon is deflated and the catheter is proximally withdrawn from the patient.

Approximately 300,000 PTCA procedures were performed in the United States in 1990 and nearly one million procedures worldwide in 1997. The increasing popularity of the PTCA procedure is attributable to its relatively high success rate, and its minimal invasiveness compared with coronary by-pass surgery. Patients treated by PTCA, however, suffer from a high incidence of restenosis, with about 35% or more of all patients requiring repeat PTCA procedures or by-pass surgery, with attendant high cost and added patient risk. Other revascularization procedures such as laser angioplasty and rotational atherectomy appear to also trigger a restenosis initiating response.

Recent attempts to prevent restenosis by use of drugs, mechanical devices, and other experimental procedures have had limited long term success. Stents, for example, dramatically reduce acute reclosure, and slow the clinical effects of smooth muscle cell proliferation by enlarging the minimum luminal diameter, but otherwise do nothing to slow the proliferative response to the angioplasty induced injury.

Restenosis is now believed to occur at least in part as a result of injury to the artenal wall during the lumen opening angioplasty procedure. In some patients, the injury initiates a repair response that is characterized by hyperplastic growth of the vascular smooth muscle cells in the region traumatized by the angioplasty. Intimal hyperplasia or smooth muscle cell proliferation narrows the lumen that was opened by the angioplasty, regardless of the presence of a stent, thereby necessitating a repeat PTCA or other procedure to alleviate the restenosis.

Preliminary studies indicate that intravascular radiotherapy (IRT) has promise in the treatment or long-term control of restenosis following angioplasty. IRT may also be used to prevent or delay stenosis following cardiovascular graft procedures or other trauma to the vessel wall. Proper control of the radiation dosage, however, appears to be important to inhibit or arrest hyperplasia without causing excessive damage to healthy tissue. Overdosing of a section of blood vessel can cause arterial necrosis, inflammation and hemorrhaging. Underdosing will result in inadequate inhibition of smooth muscle cell hyperplasia, or even exacerbation of hyperplasia and resulting restenosis. Thus, a variety of radiation delivery devices have been devised.

U.S. Pat. No. 5,059,166 to Fischell discloses a radioactive stent that is permanently implanted in the blood vessel after completion of the lumen opening procedure. Close control of the radiation dose delivered to the patient by means of a permanently implanted stent is difficult to maintain because the dose is entirely determined by the activity of the stent at the particular time it is implanted. In addition, current stents are generally not removable without invasive procedures. The dose delivered to the blood vessel is also non-uniform because the tissue that is in contact with the individual strands of the stent receive a higher dosage than the tissue between the individual strands. This non-uniform dose distribution may be especially disadvantageous if the stent incorporates a low penetration source such as a beta emitter.

Another approach which is both removable and self centering is the radiation delivery balloon. See, for example, U.S. Pat. No. 5,782,742 to Crocker et al. and U.S. Pat. No. 5,947,889 to Hehrlein in which the isotope is carried by the balloon. A variation in which the balloon is filled with a radioactive liquid is disclosed in U.S. Pat. No. 5,616,114 to Thornton et al.

A third approach involves the use of wire sources in which the isotope is carried by a flexible wire or wire like structure. Examples include U.S. Pat. No. 5,199,939 to Dake et al. and U.S. Pat. No. 5,833,593, among others, to Liprie. Used alone, the wire type sources tend to lie off axis in the vessel, producing different delivered dose characteristics in the near wall and the far wall due to absorption and penetration issues. Thus, a variety of centering catheters or structures have been devised in an effort to center the source in the lumen. Unfortunately, centering catheters in general add to the crossing profile of the device and possibly also limit its ability to track through small diameter and/ or tortuous vascular pathways.

Thus, notwithstanding the various efforts in the prior art, there remains a need for an access and/or centering catheter for wire and wire type sources which minimizes the catheter crossing profile while permitting rapid placement and centering of a radioactive source wire at the treatment site.

SUMMARY OF THE INVENTION

There is provided in accordance with one aspect of the present invention, a low profile radioactive wire placement catheter. The catheter comprises an elongate, flexible, tubular body, having a proximal section and a distal section. An outer tubular wall in the distal section contains a guidewire lumen and a collapsible, closed end radioactive wire placement lumen. An inner flexible wall extends through the outer tubular wall and separates the guidewire lumen from the closed end radioactive wire placement lumen.

Preferably, the proximal section is separated from the distal section by a transition, which is positioned in between the proximal end and the distal end of the catheter. Preferably, the transition is positioned within the range of from about 4 cm to about 40 cm from the distal end of the catheter. The outside diameter of the catheter in the distal section is preferably smaller than the outside diameter of the catheter in the proximal section. In one embodiment, a centering structure such as one or more centering balloons is carried by the catheter and communicates with the proximal end of the catheter through a centering lumen.

In accordance with another aspect of the present invention, there is provided a method of delivering radiation to a site within a patient. The method comprises the steps of providing a catheter having a distal section in which a first lumen and a second lumen are separated by a flexible wall. A guidewire is advanced through the patient to the site. The catheter is advanced along the guidewire to the site, with the guidewire extending through the second lumen. The first lumen, second lumen and guidewire are dimensioned such that when the guidewire is positioned within the second lumen, the first lumen is substantially collapsed. The guidewire is withdrawn proximally from at least the distal section of the catheter, and a radiation delivery wire is introduced through the first lumen to treat the site.

The catheter comprises a transition between the proximal section and the distal section, and the withdrawing the guidewire step comprises withdrawing the distal end of the guidewire to a position between the distal end of the transition and the proximal end of the catheter. Preferably, the withdrawing the guidewire step comprises withdrawing the distal end of the guidewire to a point within the range of from about 3 cm to about 40 cm from the distal end of the catheter.

In one embodiment, the method further comprises the steps of retracting the radiation delivery wire from the distal section, and readvancing the guidewire distally through the distal section across the treatment site. The catheter may thereafter be proximally withdrawn from the patient, while leaving the guidewire in place across the site. In one embodiment, the introducing a radiation delivery wire and retracting the radiation delivery wire steps are accomplished using an afterloader.

In accordance with a further aspect of the present invention, there is provided a method of positioning a radiation source at a site within a patient. The method comprises the steps of providing a catheter having a guidewire lumen and a radiation delivery lumen. The catheter is advanced along a guidewire to the site. The guidewire is retracted such that at least a distal portion of the catheter extends distally beyond a distal end of the guidewire. The guidewire lumen is collapsed in the distal portion of the catheter, and the radiation source is introduced into the radiation delivery lumen. In one embodiment, the guidewire lumen in the distal portion of the catheter collapses in response to distal advancement of the radiation source.

In accordance with a further aspect of the present invention, there is provided a radiation delivery catheter for temporarily placing an isotope at a treatment site within a patient. The catheter comprises an elongate flexible body having a proximal end and a distal end. A transition on the body is positioned within the range of from about 2 cm to about 50 cm from the distal end. At least a guidewire lumen and a radiation source wire lumen are positioned in the body, distal of the transition, the guidewire lumen and the radiation source wire lumen separated by a flexible wall. The flexible wall is moveable between a first position to allow a guidewire to be advanced through the guidewire lumen, and a second position to allow a radiation source wire to be advanced through the radiation source wire lumen.

Preferably, the outside diameter of catheter distal of the transition is no more than about 110% of the sum of the diameters of the guidewire lumen when the wall is in the first position and the radiation source wire lumen when the wall is in the second position.

The tubular body preferably comprises a tubular outer wall defining an interior, and the interior is divided into at least the guidewire lumen and the radiation source wire lumen by the flexible wall. At a cross section through a distal portion of the catheter, a first lateral end of the flexible wall is connected to the outer wall at a first point, and a second lateral end of the flexible wall is connected to the outer wall at a second point to define the guidewire lumen and the radiation source wire lumen on either side of the flexible wall. The lateral width of the flexible wall from the first point to the second point is preferably greater than the linear distance between the first point and the second point. Preferably, the width is at least about 115% of the linear distance between the first point and the second point. In some embodiments, the width is at least about 130% of the linear distance between the first point and the second point.

Preferably, the delivery catheter further comprises a centering element near the distal end. In one embodiment, the centering element comprises at least one inflatable balloon. Two or more inflatable balloons may be provided, arranged to center at least a portion of the catheter in a vessel, while simultaneously permitting perfusion through the vessel.

In accordance with a further aspect of the present invention, there is provided a method of delivering a dose of radiation to a site in a vessel. The method comprises the steps of advancing a catheter along a guidewire to a site in a vessel. The guidewire is partially retracted from the catheter, and a radioactive source wire is distally advanced through the catheter to treat the site.

The proximally retracting the guidewire step comprises retracting the guidewire until a visual indium appears. Preferably, the visual indium comprises a color change or stripe on the guidewire which becomes visible at the proximal end of the catheter when the distal end of the guidewire has been retracted a predetermined distance into the catheter.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 1 is a side elevational view of an over the wire embodiment of a radioactive wire placement catheter in accordance with the present invention.

FIG. 2 is a side elevational view of an alternate over the wire embodiment having a centering balloon.

FIG. 3 is a cross-sectional view taken along the line 3—3 in FIG. 1.

FIG. 4A is a cross-sectional view taken along the line 4—4 in FIG. 1, schematically illustrating a coaxial distal dual lumen configuration.

FIG. 4B is a cross-sectional view as in FIG. 4A, illustrating a guidewire or a radiation wire in the central lumen.

FIG. 4C is a cross-sectional view as in FIG. 4B, with the wall of the central lumen collapsed following proximal withdrawal of the wire to maximize the cross-sectional area of the outer lumen.

FIG. 4D is a cross-sectional view taken along the line 4—4, in FIG. 1, schematically illustrating a side-by-side distal dual lumen configuration.

FIG. 4E is a cross sectional view as in FIG. 4D, illustrating a guidewire in a first lumen.

FIG. 4F is a cross-sectional view as in FIG. 4D, with a second lumen in an enlarged orientation.

FIG. 5 is a cross-sectional view through a rapid exchange embodiment of a radioactive wire placement catheter in accordance with the present invention.

FIG. 6 is a cross-sectional fragmentary view through a distal portion of the catheter of FIG. 5, illustrating a guidewire positioned within the guidewire lumen.

FIG. 7 is a fragmentary cross-sectional view as in FIG. 6, with the guidewire retracted from the distal portion of the guidewire lumen.

FIG. 8 is a fragmentary cross-sectional view as in FIG. 6, with the guidewire retracted from the distal segment of the guidewire lumen, and a radioactive wire positioned within the distal segment of the closed end collapsible radioactive wire lumen.

DETAILED DESCRIPTION OF PREFERRED EMBODIMENTS

Referring to FIG. 1, there is disclosed a catheter 10 in accordance with one aspect of the present invention. Although primarily described in the context of a radioactive wire placement catheter without a centering element, catheters of the present invention can readily be modified to incorporate centering structures, angioplasty balloons, temporary stent, perfusion, radiation delivery, drug delivery, stent placement or stent sizing features, some of which are discussed below, or any combination of these features, as will be readily apparent to one of skill in the art in view of the disclosure herein.

The catheter 10 generally comprises an elongate tubular body 16 extending between a proximal end 12 and a distal functional end 14. The length of the tubular body 16 depends upon the desired application. For example, lengths in the area of about 120 cm to about 140 cm are typical for use in femoral access percutaneous transluminal coronary angioplasty applications. Intracranial applications may call for a different catheter shaft length depending upon the vascular access site, as will be apparent to those of skill in the art.

In the illustrated embodiment, the tubular body 16 is divided into at least a proximal section 33 and a distal section 34 separated by a transition 32, discussed infra. Alternatively, the moveable wall or the collapsible inner tube within an outer tube construction of distal section 34 can extend the entire length of the catheter from the manifold 18 or proximal connector to distal tip 25, as will become apparent from the disclosure herein.

The proximal section 33 of tubular body 16 may be produced in accordance with any of a variety of known techniques for manufacturing balloon-tipped catheter bodies. such as by extrusion of appropriate biocompatible polymeric materials. Known materials for this application include high and medium density polyethylenes, polytetrafluoroethylene, nylons, and a variety of others such as those disclosed in U.S. Pat. No. 5,499,973 to Saab, the disclosure of which is incorporated in its entirety herein by reference. Alternatively, at least a proximal portion or all of the length of tubular body 16 may comprise a spring coil, solid walled hypodermic needle tubing, or braided reinforced wall, as is understood in the catheter and guidewire arts.

The distal section 34 and in some embodiments the proximal section 33 as well can be constructed in accordance with any of a variety of known microcatheter shaft designs, to retain trackability and resist kinking while minimizing the O.D. Single lumen microcatheters can be converted to a dual or multiple lumen form by positioning a collapsible tube within the lumen and modifying the manifold and distal ends accordingly, to produce the configuration illustrated in FIGS. 4A–4C, discussed below.

For most applications, the proximal section 33 of tubular body 16 is provided with an approximately circular cross-sectional configuration having an external diameter within the range of from about 0.025 inches to about 0.065 inches. In accordance with one embodiment of the invention, the proximal section 33 of tubular body 16 has an external diameter of about 0.042 inches (3.2 f) throughout most of its length. Alternatively, a generally oval or triangular cross-sectional configuration can also be used, as well as other noncircular configurations, depending upon the method of manufacture, number and arrangement of internal lumens and the intended use.

In a catheter intended for peripheral vascular applications, the proximal section 33 of body 16 will typically have an outside diameter within the range of from about 0.039 inches to about 0.065 inches. In coronary vascular applications, the proximal section 33 of body 16 will typically have an outside diameter within the range of from about 0.025 inches to about 0.045 inches. The illustrated construction of distal section 34 permits lower external cross-sections, as low as 0.028 inches or 0.025 inches or 0.022 inches or lower as may be desired for remote coronary or intracranial applications.

Low diameter shafts in accordance with the present invention may also be dimensioned for use in ureters, Fallopian tubes and other lumens and potential lumens, as well. Rigid external walled devices such as for IV catheterization, solid tissue access or puncture (e.g. laparoscopic tools) may also utilize the flexible internal divider wall or walls or tube within a tube construction of the present invention to optimize the number and/or size of two or more distinct functional lumen within a minimal outside diameter.

Diameters outside of the preferred ranges may also be used, provided that the functional consequences of the diameter are acceptable for the intended purpose of the catheter. For example, the lower limit of the diameter for any portion of tubular body 16 in a given application will be a function of the number of fluid or other functional lumen contained in the catheter, together with the acceptable minimum flow rate of dilatation fluid or drugs to be delivered through the catheter, and the desired structural integrity.

Tubular body 16 must have sufficient structural integrity (e.g., column strength or "pushability") to permit the catheter to be advanced to distal locations without buckling or undesirable bending of the tubular body. The ability of the body 16 to transmit torque may also be desirable, such as to avoid kinking upon rotation, to assist in steering, and in embodiments having a drug delivery capability on less than the entire circumference of the delivery balloon. The tubular body 16, and particularly the distal section 34, may be provided with any of a variety of torque and/or column strength enhancing structures. or example, axially extending stiffening wires, spiral wrapped support layers, braided or woven reinforcement filaments may be built into or layered on the tubular body 16 particularly in the distal section 34. See, for example, U.S. Pat. No. 5,891,114 to Chien, et al., the disclosure of which is incorporated in its entirety herein by reference.

Larger diameters generally have sufficient internal flow properties and structural integrity, but reduce perfusion in the artery in which the catheter is placed. Increased diameter catheter bodies also tend to exhibit reduced flexibility, which can be disadvantageous in applications requiring advancement of the distal end of the catheter through highly tortuous pathways. In addition, lesions requiring treatment are sometimes located in particularly small diameter arteries, necessitating the lowest possible profile.

The proximal end 12 of catheter 10 is provided with a manifold 18 having one or more access ports as is known in the art. Generally, manifold 18 in a wire placement catheter without an inflatable centering structure is provided with a guidewire port 20 in an over-the-wire construction and a radioactive source introduction port 22. Manifold 18 may be injection molded from medical grade plastics or formed in accordance with other techniques known in the art.

Additional access ports are provided as needed, depending upon the functional capabilities of the catheter. For example, in a balloon centered embodiment, an inflation port 23 is placed in fluid communication with one or more inflatable balloons 24 by wary of an inflation lumen extending throughout the tubular body 16 as is known in the art.

The distal end 14 of a wire placement catheter 10 with a centering structure may be provided with an inflatable balloon 24, shown schematically in FIG. 2. However, in embodiments intended solely for nonballoon applications such as access catheters or nonballoon centering catheters, the balloon 24 may be omitted. Any of a variety of centering structures can readily be added to the radioactive wire placement catheter of the present invention, including those disclosed in U.S. Pat. No. 5,797,948, issued Aug. 25, 1998 to Dunham, U.S. Pat. No. 5,851,171 issued Dec. 22, 1998 to Gasson, U.S. Pat. No. 5,910,101 issued Jun. 8, 1999 to Andrews et al., and U.S. Pat. No. 5,938,582 issued Aug. 17, 1999 to Ciamacco Jr. et al., the disclosures of which are incorporated in their entireties herein by reference.

The distal end 14 of the catheter 10 is further provided with an atraumatic distal tip 25 usually having a guidewire exit port 26 as is known in the art. Preferably, one or more radiopaque markers (not illustrated) are provided on the catheter body 16 to facilitate positioning of the catheter as is known in the art. Suitable marker bands can be produced from a variety of materials, including platinum, gold, and tungsten/rhenium alloy.

The distal tip 25 may be axially separated from the balloon 24 by a distal introduction segment having an outside diameter within the range of from about 0.014 inches to about 0.030 inches, and a length within the range of from about 2 mm to about 5 mm. In one embodiment, the introduction segment has an outside diameter of about 0.020 inches, and a length of about 2.0 mm.

Referring to FIG. 3, there is illustrated a cross-sectional view through the proximal section 33 of the catheter shaft 16 of the embodiment of FIG. 1. In the illustrated embodiment, the proximal section 33 comprises an extrusion, having a guidewire lumen 28 and a radioactive wire lumen 30. Alternatively, the proximal section 33 can be formed having a concentric configuration if desired.

In many applications, the proximal section 33 will not be required to traverse particularly low profile or tortuous arteries. For example, in a typical PTCA application, the proximal section 33 will extend from a position outside of the patient distally through the guide catheter. Outside diameters of the proximal section 33 within the range of from about 0.03 inches to about 0.06 inches are generally suitable for this application. For this reason, any of a variety of known catheter shaft constructions, such as polymeric extrusions and hypotubes can be utilized for the proximal section 33.

In the illustrated embodiment, the proximal section 33 is separated from a distal section 34 by a transition 32. In the design illustrated in FIGS. 4A–4C, the side-by-side lumen configuration of the proximal section 33 converts in the transition 32 to a coaxial like orientation in the distal section 34. Alternatively, the distal section 34 in the embodiments of FIGS. 4D–4F, includes a side by side construction. The catheter can readily be constructed utilizing a concentric or side by side configuration throughout its entire length in view of the disclosure herein.

Referring to FIGS. 4A–4C, there is illustrated the collapsible interior wall feature of the present invention which permits a minimal outside diameter of the catheter shaft 16 at least in the distal section 34. Referring to FIG. 4A, an interior tubular wall 38 defies a central lumen 28. Central lumen 28 is referred to herein as the guidewire lumen, however, the central lumen 28 can be alternatively utilized for the radiation wire, inflation media, drug delivery or other communication depending upon the catheter design.

The inner tubular wall 38 defining a first lumen such as guidewire lumen 28 is positioned within an outer tubular wall 36. The outer wall 36 is illustrated as though it is spaced radially outwardly apart from the inner wall 38 to exaggerate a potential annular space 30 therebetween. Annular space 30 in the illustrated embodiment is enlarged and utilized as a second lumen such as the radioactive source lumen. However, as will become apparent in view of the disclosure herein, the inner wall 38 when in its enlarged interior cross-sectional area configuration may completely or substantially fill the area within outer wall 36, which space is generally not necessary during the catheter placement step. In this manner, the shaft OD can be minimized by reducing the radioactive source lumen 30 to a potential lumen when the inner wall 38 is filled by the guidewire. Following positioning of the catheter at a treatment site, and proximal withdrawal of the guidewire from at least a distal portion of inner wall 38, that distal portion of wall 38 can collapse the guidewire lumen to produce an isolated radioactive wire lumen without affecting the OD of the catheter shaft.

Referring to FIG. 4B, a guidewire 40 is illustrated as positioned within the guidewire lumen 28 defined by inner tubular wall 38. As can be appreciated by those of skill in the art, the diameter of the guidewire 40 is illustrated as slightly smaller (e.g., by about 0.001–0.003 inches) than the inside diameter of the tubular wall 38. Avoiding a tight fit between the guidewire 40 and inside diameter of guidewire lumen 28 enhances the slideability of the catheter over the guidewire. In ultra small diameter catheter designs, it may be desirable to coat the outside surface of the guidewire 40 and/or the inside surface of the inner tubular wall 38 with a lubricous coating to minimize friction as the catheter 10 is axially moved with respect to the guidewire 40. A variety of coatings may be utilized, such as Paralene, Teflon, silicone rubber, polyimide-polytetrafluoroethylene composite materials or others known in the art and suitable depending upon the material of the guidewire or inner tubular wall 38.

In FIGS. 4A and 4B, the inner tubular wall 38 is illustrated in an open, enlarged cross-sectional area configuration. In the open configuration, the outside diameter of inner tubular wall 38 may substantially fill the inside diameter of outer tubular wall 36. Alternatively, the inner tubular wall 38 may be spaced radially inwardly from the outer tubular wall 36 as illustrated. Some available cross-sectional area for lumen 30 even in the collapsed configuration may be desirable in embodiments such as illustrated in FIGS. 6–8 of parent application Ser. No. 09/299,177, filed Apr. 23, 1999, the disclosure of which is incorporated in its entirety herein by reference. In this design, a removable column support can fit in the inflation lumen during catheter placement.

Referring to 4C, the inner tubular wall 38 is illustrated in a collapsed, minimized interior cross-sectional area orientation following removal of guidewire 40. The effect of collapsing the inner tubular wall 38 as illustrated is to enlarge the available cross-sectional area of the second lumen 30 without the need to change the OD of the distal catheter section 34. The inner tubular wall 38 may collapse under its own bias, such as by providing the wall 38 with a folded preset during the catheter fabrication process. Alternatively, elastic materials can be utilized to retract the inner tubular wall 38 to a reduced cross-sectional area when not filled with the guidewire or pressurized media. Preferably, the inner tubular wall 38 is constructed from a sufficiently flexible and thin substantially inelastic material that the inner tubular wall 38 folds or collapses in response to introduction of inflation media, a radioactive wire, or other material into second lumen 30.

The catheter shaft of the present invention can be constructed in any of several basic configurations. Selection of a particular one will depend primarily upon the length of the catheter which is expected to traverse a particularly low diameter or tortuous pathway.

For coronary vascular applications, for example, the proximal section 33 will be mostly or entirely within the relatively large diameter guide catheter. The transition 32 can be located on the catheter shaft 16 to correspond approximately with the distal end of the guide catheter when the balloon 24 and/or distal end 14 is at the treatment site. Viewed the other way, the length of the distal section 34 is preferably at least as long as the distance from the ostium of the relevant coronary artery to the treatment site. In most applications, the transition 32 will be at least about 3 cm, preferably at least about 5 cm and alternatively as much as about 10 cm but not more than about 20 cm from the distal end of the catheter. Distances as much as 30 cm to 50 cm or greater between the transition 32 and distal end of the catheter may also be desirable in some applications.

For certain other applications, such as intracranial catheterizations, the distal section is preferably at least about 5 cm long and small enough in diameter to pass through vessels as low as 3 mm or 2 mm or lower. Catheters for this application may have a proximal section length of between about 60 cm to about 150 cm and a distal section length of between about 5 cm to about 15 cm, and the distal section is able to track a tortuous path of at least about 5 cm through vessels of less than about 3 mm lumen ID. further structure, dimensional and method disclosure can be found in U.S. Pat. No. 4,739,768 to Engelson, the disclosure of which is incorporated in its entirety herein by reference.

As an alternative to the illustrated embodiment, the flexible wall configuration can be utilized throughout the length of the catheter shaft, from the proximal manifold through the distal end. In a tube within a tube embodiment, the outer tube may comprise an extrusion using materials such as those disclosed previously herein, and a wall thickness sufficient to provide a reasonable degree of pushability. For example, a HDPE tube having an OD within the range of from about 0.024 inches to about 0.032 inches may have a wall thickness of about 0.003 inches. This "pushable" coaxial outer tube embodiment can alternatively have dissimilar proximal and distal sections such as a proximal hypotube section and a distal extrusion. A highly flexible, thin walled inner tube 38 extends throughout the length of the catheter in this embodiment. Wall thicknesses on the order of 0.001 inches or 0.0005 or less are preferred, to minimize catheter profile and ensure collapsibility such as following proximal withdrawal of the guidewire to optimize the cross-sectional area of the radiation wire lumen. Alternatively, very thin walled tubing can be used for the outer tube in either the distal section or throughout the length of the catheter, in addition to a very thin walled inner tube 38.

Coaxial multilumen catheters known in the art generally are not available having a cross-section of much less than about 0.030 inches. Use of the configuration illustrated in FIGS. 1–8, however, can permit a catheter to have an outside diameter in at least its distal section 34 of as low as about 0.006 inches or 0.008 inches greater than the diameter of the guidewire 40. In general, this is accomplished by the flexible wall of the present invention, which permits greater than 50% of the interior cross-sectional area to be used for the guidewire, and then, by withdrawal of the guidewire, greater than 50% of the interior cross-sectional area to be used for the inflation lumen.

For many conventional PTCA procedures, guidewires having an outside diameter the range of from about 0.009 inches to about 0.015 inches are used. When used with a 0.010 inch guidewire, for example, the catheter 10 of the present invention can be constructed utilizing an inner tube 38 having a wall thickness of about 0.001 inches, an inside diameter of about 0.012 inches, and an outside diameter of about 0.014 inches. In a minimum outside diameter embodiment, the outer tubular wall 36 may have an inside diameter of about 0.014 inches, and a wall thickness sufficient for the particular construction material to provide adequate pushability for the catheter. For many applications, this may be accomplished having an outer wall 36 thickness within the range of from about 0.002 inches to about 0.006 inches.

Thus, in the foregoing example, a wall thickness of about 0.003 inches will produce a catheter shaft with an OD of about 0.020 inches. When the guidewire extends through the inner tube 38, the ID of the inner tube is from 0.010 to 0.012 inches. Following withdrawal of the guidewire and introduction of a radioactive wire into second lumen 30, the inner tube 38 will collapse to leave a second lumen 30 with a cross-sectional area roughly equivalent to that of a 0.010 inch–0.012 inch diameter lumen without any expansion of the OD of the catheter shaft.

The flexible wall lumen divider of the present invention can be used to separate a flow directed balloon lumen from a drug or contrast media or embolic material delivery lumen for flow directed access in which column strength may be less important. See, for example, U.S. Pat. No. 5,336,205 to Zenzen, et al., the disclosure of which is incorporated in its entirety herein by reference. A flow directed balloon can be attached to the distal end of any of the catheters disclosed herein and supplied by a collapsible lumen as will be understood in view of the disclosure herein.

The collapsible lumen feature of the present invention can also readily be incorporated into a balloon centered catheter with perfusion by adding a collapsible radioactive wire lumen to the perfusion embodiment 80 described in greater detail in application Ser. No. 09/299,177. The perfusion catheter 80 includes an elongate flexible tubular body 82, having an outer tube 84 with a central lumen 86 such as for receiving a guidewire. An inner tube 88 extends axially throughout at least portion of the outer tube 84. Inner tube 88 defines a potential lumen 90, illustrated as collapsed in FIGS. 4, 6A and 7A. Potential lumen 90 provides communication with the interior 92 of a balloon 94 such as through one or more inflation ports 96 for inflation of the balloon 94. A radiation wire lumen extends throughout the length of the catheter.

A perfusion lumen 100 extends axially between at least one proximal perfusion port 102 and one or more distal perfusion ports 104. Perfusion lumen 100 provides perfusion from a proximal side of the balloon 94 to the distal side of the inflation port 96. In this manner, blood may perfuse through the proximal perfusion port 102, along perfusion lumen 100, through perfusion ports 104, and through the distal portion of central lumen 86 while the inner tube 88 is enlarged (by unfolding or stretching) to accommodate the introduction of inflation media into the interior 92 of balloon 94.

Following positioning of the balloon 94 at the treatment site, the guidewire is retracted proximally to leave at least a distal portion of central lumen 86 unoccupied. Inflation media is thereafter introduced through inner tube 88, causing inner tube 88 to expand to provide inflation media access by way of potential lumen 90 to the interior 92 of balloon 94. Once centered in the vessel, the radiation delivery wire is advanced through the collapsible radiation wire lumen in the distal segmnent of the catheter, such as by expanding the collapsible radiation delivery wire lumen into the guidewire lumen.

Referring to FIGS. 4D–8, there is illustrated an embodiment of the present invention in which the inner flexible wall is formed integrally with the outer tubular body to separate two or more lumen in a side-by-side orientation. Referring, for example, to FIG. 5, there is illustrated a side elevational cross section of a rapid exchange embodiment of a low profile radioactive wire placement catheter in accordance with the invention. The catheter 10 generally comprises a proximal end 12 and a distal end 14 having a tubular body 16 extending therebetween. The catheter is illustrated as having a proximal section 33 and a distal section 34 separated by a transition 32 as has been discussed in connection with previous embodiments.

Throughout the length of the catheter there is provided at least a radioactive wire lumen 30. Throughout at least a distal portion of the tubular body 16 there is additionally provided a guidewire lumen 28. Guidewire lumen 28 may terminate in a proximal guidewire exit port 29 in-between the proximal end 12 and distal end 14 of the tubular body 16, preferably in the range of from about 10 cm to about 40 cm from the distal end 14. Alternatively, the proximal guidewire exit port may be positioned on the manifold in an over the wire embodiment, by extending the guidewire lumen 28 proximally throughout the length of the catheter shaft.

The catheter is provided with a flexible wall 120, which separates the guidewire lumen 28 from the radiation wire lumen 30. As illustrated schematically in FIGS. 6–8, at least a portion of the distal section 34 in a simple two-lumen embodiment comprises an outer tubular wall 36 containing a guidewire lumen 28 and radiation lumen 30 separated by a flexible wall 120. The flexible wall 120 has a transverse thickness which is sufficiently thin given the construction material to permit the wall 120 to move between a first position as illustrated in FIG. 6 and a second position as illustrated in FIG. 8. This construction can readily be incorporated into catheters having an angioplasty balloon, centering balloon or other centering structure with or without perfusion. Thicknesses for the flexible wall 120 on the order of about 0.002" and less are contemplated, and thicknesses on the order of no more than about 0.001" are preferred, depending upon the material and construction technique. Drawn bump tubing or drawn down straight extrusion stock may have a wall 120 thickness as low as about 0.0005 or less.

The flexible wall 120 also has a width in the transverse direction between a first attachment point 122 and a second attachment point 124 to the outer wall 36. As illustrated, the transverse width of the flexible wall 120 is preferably greater than the inside diameter of the tubular outer wall 36 e.g., linear distance between first attachment point 122 and second attachment point 124 in a circular cross section embodiment). Transverse widths for flexible wall 120 of at least about 110% or 120%), and in some embodiments at least about 140% of the inside diameter of the outer wall 36 may be used. For materials which are substantially inelastic in the thicknesses provided for flexible wall 120, a transverse width of flexible wall 120 which approximates one-half of the inside circumference of the outer wall 36 will optimize the profile reducing advantages of the present invention as illustrated schematically in FIGS. 4E and 4F.

The flexible wall is illustrated as extending radially inwardly at about 90° from the surface of the wall 36 at attachment points 122 and 124. That angle may desirably be increased to as much as 110° or 145° or more in the direction of the radiation wire lumen to optimize (minimize friction in) the guidewire lumen, or in the direction of the guidewire lumen to optimize the radiation wire lumen.

As illustrated in FIGS. 4E and 4F, the flexible wall 120 is movable between a first concave position in which the guidewire lumen 28 is optimized and the radiation wire lumen 30 is minimized, and a second oppositely concave position in which the radiation wire lumen 30 is optimized and the guidewire lumen 28 is minimized. This permits sequential use of the two lumen with a minimum outside diameter, as has been discussed. In general, although this embodiment of the invention is illustrated as having only a first and second lumen separated by a flexible wall 120, three or four or more collapsible interior lumen can readily be provided in accordance with the present invention as will be apparent to those of skill in the art in view of the disclosure herein. Alternatively, at least two collapsible lumen can be combined with at least one non collapsible lumen if desired.

A collapsible "blind" lumen with a sealed distal end can be provided in either a balloon or nonballoon embodiment, for receiving a radioactive wire or seed train to deliver radiation to a treatment site such as following angioplasty and/or within a stent. The distal end of either the first lumen 28 or the second lumen 30 can be closed and sealed to provide a sealed source radiation wire lumen in any of a variety of ways, depending upon the construction materials. For example, the distal end of inner tubular wall 38 can be compressed and heat bonded to itself, or provided with an adhesive plug. The second lumen 30 can be sealed by providing an annular bond between the distal ends of the inner tube 38 and outer tube 36. In the embodiment of FIGS. 4D–4F, either of the side by side lumen can be closed by heat bonding, adhesives, tie layers or other known bonding techniques to provide a bond 126. Alternatively, the distal ends of both lumen can be left open, such as in a low profile access catheter application.

The distal section 34, or any portion of the catheter having the flexible wall 120, may be manufactured as an extrusion such that the flexible wall 120 is integrally formed with the outer wall 36. In one method of manufacture, the extrusion is formed from a medium to high melt index polyethylene or other polymer having an outside diameter of greater than the diameter of the desired finished product. The raw extrusion can thereafter be drawn down to the desired diameter, in accordance with known processing techniques. The draw down pull speed can be varied such as along a proximal portion of the extrusion to produce a taper to a larger proximal diameter. This permits a smooth transition 32 from the relatively smaller outside diameter distal section 34 to the typically larger outside diameter of proximal section 33. High melt index materials allow the production of a greater number of different diameter draw downs by adjusting pull speed and other process parameters, for a given set of tooling as will be appreciated by those of skill in the art. The distal end 14 can be further reduced in diameter by an additional draw down step if desired.

The extrusion containing the flexible wall 120 can be assembled onto the distal end of a proximal section 33 in accordance with any of a variety of techniques which will be apparent to those of skill in the art. Manufacturing techniques are discussed in greater detail in application Ser. No. 09/299,177.

The radioactive wire placement catheter in accordance with the present invention can be utilized to direct and center any of a wide variety of radioactive sources which are known in the art. For example, radioactive gamma emitter wires are disclosed in U.S. Pat. No. 5,503,613 issued Apr. 2, 1996 to Wienberger, U.S. Pat. No. 5,618,266 issued Apr. 8, 1997 to Liprie, and U.S. Pat. No. 5,857,956 issued Jan. 12, 1999 to Liprie, the disclosures of which are incorporated in their entireties herein by reference. In general, one or more radioactive seeds or pellets 128 may be provided on or near the distal end of a flexible wire. Alternatively, a portion of the radioactive wire may be constructed from an isotope. Gamma radiation sources which can be utilized for these purposes include cesium 137, cobalt 60, iodine 125, iodine 131, cobalt 57, iridium 192, gold 198, palladium 103 and others which will be known in the art. Beta emitters may also be used, particularly in small vessels due to the known penetration characteristics of beta radiation. The low profile of the present invention may be particularly well suited to access currently untreated (e.g., less than about 2 mm or 1.5 mm) vessels for radiation treatment, in which beta radiation may be preferable over gamma.

Preferably, the activity and isotope characteristics will be selected such that treatment times within the range of from about 2 to 5 minutes to no more than about 30 minutes would be necessary. The length of the radioactive zone on the radiation wire is preferably selected to deliver a radioactive dose along a segment of vessel which is greater in axial length than the axial length of the underlying lesion. Thus, radioactive segments having a length within the range of from about 2 cm to about 10 cm are presently contemplated.

When used for placing a radioactive wire having a beta emitter, such as phosphorous 32, radiation shielding can be accomplished using fairly simple and understood shielding techniques. However, in view of the deeper penetration of gamma radiation, certain steps such as introduction of the radioactive wire into the blind lumen are desirably performed on an automated basis so that clinical personnel can leave the room or be protected behind suitable shielding structures. For this purpose, a computer controlled afterloader, such as that distributed by Nucletron Corp. of Columbia, Md., may be customized and connected to the proximal end of the radiation wire placement catheter, and utilized to advance the radiation dose delivery wire into the blind lumen until the radioactive source on the wire is adjacent the target area. The afterloader may additionally be programmed to oscillate the radioactive wire axially within the lumen, to axially extend the effective dose delivery length of the source, and accomplish additional dosing requirements. The afterloader may also be programmed to "step" the source axially through the treatment zone for predetermined times at each stop. In this manner, a relatively short (e.g. 1 cm–5 cm) source can treat a much longer treatment zone. Afterloaders may be modified for the present purpose in accordance with the disclosure of U.S. Pat. No. 5,503,613, which has previously been incorporated by reference.

Although the present invention has been described in terms of certain preferred embodiments, it may be incorporated into other embodiments by persons of skill in the art in view of the disclosure herein. The scope of the invention is therefore not intended to be limited by the specific embodiments disclosed herein, but is intended to be defined by the full scope of the following claims.

What is claimed is:

1. A method of delivering radiation to a site within a patient, comprising the steps of:

providing a catheter having a distal section in which a first lumen and a second lumen are separated by a flexible wall;

advancing a guidewire through the patient to the site;

advancing the catheter along the guidewire to the site, with the guidewire extending through the second lumen, wherein the first lumen, second lumen and guidewire are dimensioned such that when the guidewire is positioned within the second lumen, the first lumen is substantially collapsed;

withdrawing the guidewire proximally from at least the distal section of the catheter; and introducing a radiation delivery wire through the first lumen to treat the site.

2. A method as in claim 1, wherein the catheter comprises a transition between the proximal section and the distal section, and the withdrawing the guidewire step comprises withdrawing the distal end of the guidewire to a position between the distal end of the transition and the proximal end of the catheter.

3. A method as in claim 2, wherein the withdrawing the guidewire step comprises withdrawing the distal end of the guidewire to a point within the range of from about 3 cm to about 40 cm from the distal end of the catheter.

4. A method as in claim 3, wherein the withdrawing the guidewire step comprises withdrawing the distal end of the guidewire to a point within the range of from about 5 cm to about 20 cm from the distal end of the catheter.

5. A method as in claim 1, further comprising the steps of retracting the radiation delivery wire from the distal section, and readvancing the guidewire distally through the distal section.

6. A method as in claim 1, further comprising the step of proximally withdrawing the catheter from the patient while leaving the guidewire at the site.

7. A method of positioning a radiation source at a site within a patient, comprising the steps of:

providing a catheter having a guidewire lumen and a radiation delivery lumen;

advancing the catheter along a guidewire to the site;

retracting the guidewire such that at least a distal portion of the catheter extends distally beyond a distal end of the guidewire;

collapsing the guidewire lumen in the distal portion of the catheter; and introducing the radiation source into the radiation delivery lumen.

8. A method as in claim 7, wherein the radiation lumen has a closed distal end.

9. A method as in claim 7, wherein the radiation source is carried by a wire.

10. A method as in claim 7, wherein the guidewire lumen in the distal portion of the catheter collapses in response to distal advancement of the radiation source.

11. A method as in claim 7, further comprising the steps of proximally retracting the radiation source and distally advancing the guidewire so that the distal end of the guidewire extends beyond the distal end of the catheter.

12. A method as in claim 11, further comprising the step of retracting the catheter from the patient while leaving the guidewire across the site.

13. A method as in claim 12, further comprising the step of advancing a second catheter along the guidewire to further treat the site.

14. A radiation delivery catheter for temporarily placing an isotope at a treatment site within a patient, comprising:

an elongate, flexible body, having a proximal end and a distal end;

a transition within the range of from about 2cm to about 50 cm from the distal end; and at least a guidewire lumen and a radiation source wire lumen in the body, distal of the transition, the guidewire lumen and the radiation source wire lumen separated by a flexible wall;

wherein the flexible wall is movable between a first position to allow a guidewire to be advanced through the guidewire lumen, and a second position to allow a radiation source wire to be advanced through the radiation source wire lumen.

15. A radiation delivery catheter as in claim 14, wherein the outside diameter of the catheter distal of the transition is no more than about 110% of the sum of the diameters of the guidewire lumen when the wall is in the first position and the radiation source wire lumen when the wall is in the second position.

16. A radiation delivery catheter as in claim 15, wherein the outside diameter of the catheter distal of the transition is no more than about the sum of the diameters of the guidewire lumen when the wall is in the first position and the radiation source wire lumen when the wall is in the second position.

17. A radiation delivery catheter as in claim 14, wherein the tubular body comprises a tubular outer wall defining an interior, and the interior is divided into at least the guidewire lumen and the radiation source wire lumen by the flexible wall.

18. A radiation delivery catheter as in claim 17, wherein at a cross section through the catheter a first lateral end of the flexible wall is connected to the outer wall at a first point and a second lateral end of the flexible wall is connected to the outer wall a second point to define the guidewire lumen and the radiation source wire lumen on either side of the flexible wall.

19. A radiation delivery catheter as in claim 18, wherein the lateral width of the flexible wall from the first point to the second point is greater than the linear distance between the first point and the second point.

20. A radiation delivery catheter as in claim 19, wherein the width is at least about 115% of the linear distance between the first point and the second point.

21. A radiation delivery catheter as in claim 19, wherein the width is at least about 130% of the linear distance between the first point and the second point.

22. A radiation delivery catheter as in claim 14, further comprising an afterloader removably coupled to the proximal end, for advancing a radioactive wire through the radiation source wire lumen.

23. A radiation delivery catheter as in claim 14, further comprising a centering element near the distal end.

24. A radiation delivery catheter as in claim 23, wherein the centering element comprises at least one inflatable balloon.

25. A radiation delivery catheter as in claim 24, wherein the centering element comprises at least two inflatable balloons, arranged to center at least a portion of the catheter in a vessel and permit perfusion through the vessel.

26. A method of delivering a dose of radiation to a site in a vessel, comprising the steps of:

advancing a catheter along a guidewire to a site in a vessel;

partially retracting the guidewire from the catheter, and distally advancing a radioactive source wire through the catheter to treat the site.

27. A method of delivering a dose of radiation as in claim 26, wherein the proximally retracting the guidewire step comprises retracting the guidewire until a visible indicium appears.

28. A method of delivering a dose of radiation as in claim 27, wherein the proximally retracting the guidewire step comprises retracting the guidewire until a color change appears on the guidewire at a proximal end of the catheter.

* * * * *